United States Patent [19]

Bütcher et al.

[11] Patent Number: 5,106,850
[45] Date of Patent: Apr. 21, 1992

[54] INDOLE DERIVATIVES

[75] Inventors: Henning Bütcher, Darmstadt; Christopy Seyfried, Seeheim-Jugenheim; Hartmut Greiner, Darmstadt, all of Fed. Rep. of Germany

[73] Assignee: Merck Patent Gesellschaft Mit Beschrankter Haftung, Darmstadt, Fed. Rep. of Germany

[21] Appl. No.: 551,816

[22] Filed: Jul. 12, 1990

[30] Foreign Application Priority Data

Jul. 13, 1989 [DE] Fed. Rep. of Germany ....... 3923045

[51] Int. Cl.$^5$ .................. A61K 31/495; C07D 413/12
[52] U.S. Cl. ..................................... 514/253; 544/368
[58] Field of Search ......................... 544/368; 514/253

[56] References Cited

U.S. PATENT DOCUMENTS 4,883,795  11/1989  Lowe III et al. .................. 544/368

FOREIGN PATENT DOCUMENTS 6713659  4/1968  Netherlands ........................ 544/368
1326833  8/1973  United Kingdom .

OTHER PUBLICATIONS

Soderpalm et al., "Effects of 5 $HT_{1A}$ Receptor Agonists and L-5-HTP in Montgomery's Conflict Test," Biochemistry & Behavior, vol. 32, pp. 259–265, Pergamon, press, 1989.

Ahlenius, Antipsychotic-like Properties of the 5-$HT_{1A}$ Agonist 8-Oh-DPAT in the Rat, Pharmacology & Toxicology, 1989, 64, 35.

Aulakh, "Food Intake, Neuroendocrine and Temperature Effects of 8-OHDPAT in the Rat," European Journal of Pharmacology, 146 (1988) 253–259.

Cervo, "Potential Antidepressant Properties of 8-hydroxy-2-(di-n-propylamino) tetralin", a Selective Serotonin$_{1A}$ Receptor Agonist, European Journal of Pharmacology, 144 (1987), 223–229.

Seyfried et al., "Biochemical and Functional Studies on EMD 49980: A Potent, Selectively Presynaptic D-2 Dopamine Agonist with Actions on Serotonin Systems," Euro. J. Phar., 160 (1989) 31–41.

Laskowski et al., Chem. Abst. 72-43733V (1970).
Sterlig Druf, Chem. Abst. 73-14684V (1970).
Sumitomo Chemical Co. Ltd. Chem. Abst. 77-164758u (1972).
Kaneko et al., Chem. Abst. 78-58465g (1973).
Ho et al. Chem. Abst. 79-13403q (1973).
Allen et al. Chem. Abst. 80-10259g (1974).
Allen et al. Chem. Abst. 84-17426a (1976).

Primary Examiner—Cecilia Shen
Attorney, Agent, or Firm—Millen, White & Zelano

[57] ABSTRACT

3-[4-(4-p-Methoxyphenylpiperazino)butyl]-5-methoxyindole and the salts thereof can be used as psychopharmaceuticals and antihypertensives.

15 Claims, No Drawings

INDOLE DERIVATIVES

SUMMARY OF THE INVENTION

The invention relates to a novel compound 3-[4-(4-p-methoxyphenylpiperazino)butyl]-5-methoxyindole (I) and the salts thereof.

BE-A 771,285 (Derwent 12863 T) includes a general formula

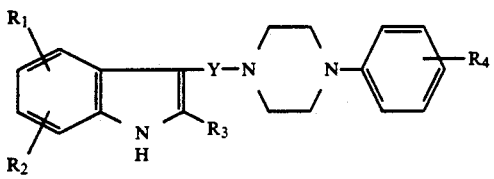

in which, inter alia, $R_1$ and $R_4$ may each be methoxy, $R_2$ and $R_3$ may each be H, and Y may be $-(CH_2)_4-$.

Furthermore, NL-A-6,713,659 (Derwent 31 566 F) indicates a general formula

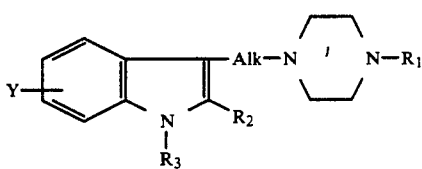

in which, inter alia, $R_1$ may be p-methoxyphenyl, $R_2$ and $R_3$ may each be H, Y may be methoxy and Alk may be $-(CH_2)_4-$.

However, the specific compound I is not mentioned in either publication.

The object of the invention was to find novel compounds capable of being used for the preparation of pharmaceuticals for the treatment of various physiological conditions.

It has been found that the compound of formula I and their physiologically acceptable acid addition salts possess valuable pharmacological properties. Thus, in particular, they are active on the central nervous system, especially as partial serotonin agonists, i.e. as an agonist or antagonist depending on the experimental model and/or the endogenous transmitter concentration. Specifically, they inhibit the binding of tritiated serotonin ligands to hippocampal receptors (Cossery et al., European J. Pharmacol. 140 (1987), 143–155). They also modify the accumulation of 5-hydroxy-tryptophan in the nuclei raphes (Seyfried et al., European J. Pharmacol. 160 (1989), 31–41) and in other cerebral areas, such as cortex, hippocampus, striatum and hypothalamus. Accordingly, the compounds are able to develop anxiolytic (Söderpalm et al., Pharmacol. Biochem. Behavior 32 (1989), 259–265), antipsychotic (Ahlenius, Pharmacol. and Toxicol. 64 (1989), 3–5), antidepressive (Cervo and Samanin, Europ. J. Pharmacol. 144 (1987), 223–229) and anorectic (Aulakh et al., Europ. J. Pharmacol. 146 (1988), 253–259) actions. They also have analgesic and hypotensive effects; thus, in catheterized, conscious, spontaneously hypertensive rats (strain: SHR/Okamoto/NIH-MO-CHB-Kisslegg; method cf. Weeks and Jones, Proc. Soc. Exptl. Biol. Med. 104 (1960), 646–648), the directly measured blood pressure is lowered after peroral administration of the compounds.

The compound I and their biocompatible acid addition salts can therefore be used as active ingredients for anxiolytics, antidepressants, neuroleptics and/or antihypertensives, and also as intermediates for the preparation of other pharmaceutically active ingredients.

The invention further relates to a process for the preparation of the indole derivative I and its salts, characterized in that a 3-(4-$X^1$-butyl)-5-methoxyindole (II) wherein $X^1$ is X or $NH_2$, and X is Cl, Br, I, OH or an OH group functionally modified to form a reactive group, is reacted with a compound of formula III $$X^2-CH_2CH_2CH(p-CH_3O-C_6H_4)-CH_2CH_2X^3 \quad \text{III}$$

wherein $X^2$ and $X^3$ can be identical or different and are each X if $X^1 = NH_2$ or are together NH in other cases, or in that a compound which conforms to I except that one or more hydrogen atoms have been replaced by one or more reducible or hydrogenolytically cleavable groups and/or one or more additional C—C and/or C—N bonds (Ia) is treated with a reducing agent, or in that a compound which conforms to I except that one hydrogen atom has been replaced by a solvolytically cleavable group (Ib) is treated with a solvolyzing agent, and/or in that a resultant base I is converted into one of its salts by treatment with an acid and/or liberated from one of its salts by treatment with a base.

The compound I is otherwise prepared by methods known per se, such as those described in the literature (e.g. in the standard works such as Houben-Weyl, Methoden der Organischen Chemie (Methods of Organic Chemistry), Georg-Thieme-Verlag, Stuttgart; Organic Reactions, John Wiley & Sons, Inc., New York; German Offenlegungsschrift 33 42 632), namely under reaction conditions such as those which are known and suitable for said reactions. It is also possible to make use of variants known per se, which are not mentioned in greater detail here.

If desired, the starting materials for the claimed process can also be formed in situ in such a way that they are not isolated from the reaction mixture but are immediately reacted further to give the compound I.

In the indole derivatives of formula II, $X^1$ is preferably X; accordingly, in the compounds of formula III, $X^2$ and $X^3$ are together preferably NH. The radical X is preferably Cl or Br, but it can also be I, OH or an OH group functionally modified to form a reactive group, especially alkylsulfonyloxy having 1–6 C atoms (e.g. methanesulfonyloxy) or arylsulfonyloxy having 6–10 C atoms (e.g. benzenesulfonyloxy, p-toluenesulfonyloxy, naphthalene-1- or -2-sulfonyloxy).

Accordingly, the indole derivative I can be obtained especially by reacting 3-(4-chlorobutyl)- or 3-(4-bromobutyl)-5-methoxyindole with 1-p-methoxyphenylpiperazine (IIIa).

Some of the compounds of formulae II and, in particular, III are known; the unknown compounds of formulae II and III can easily be prepared analogously to the known compounds. 3-(4-Hydroxybutyl)-5-methoxyindole can be obtained, for example, by reduction of 4-(5-methoxy-3-indolyl)butyric acid or esters thereof. Treatment with thionyl chloride, hydrogen bromide, phosphorus tribromide or similar halogen compounds gives the corresponding halides. The corresponding sulfonyloxy compounds can be obtained from the alcohol by reaction with the appropriate sulfonyl chlorides. 3-(4-Iodobutyl)-5-methoxyindole can be obtained, for example, by the action of potassium iodide on the relevant p-toluenesulfonates. 3-(4-Aminobutyl)-5-methoxyindole can be prepared, for example, from the halides using potassium phthalimide or by reduction of the corresponding nitriles.

The starting compound IIIa is known and can be obtained, for example, by reacting p-methoxyaniline with bis(2-chloroethyl)amine. Compounds of the formula III ($X^2$ and $X^3$ are each X) can be prepared, for example, by reduction of diesters of the formula alkyl OOC—$CH_2$—NAr—$CH_2$—COOalkyl to give diols of the formula HO—$CH_2CH_2$—NAr—$CH_2$—$CH_2$OH (III, $X^2=X^3=$OH) and, if necessary, subsequent reaction with $SOCl_2$ or $PBr_3$ (Ar=p-methoxyphenyl).

The reaction of the compounds II and III proceeds according to methods such as those known from the literature for the alkylation of amines. The components can be melted together in the absence of a solvent, in a sealed tube or an autoclave if necessary. It is also possible, however, to react the compounds in the presence of an inert solvent. Examples of suitable solvents are hydrocarbons such as benzene, toluene or xylene; ketones such as acetone or butanone; alcohols such as methanol, ethanol, isopropanol or n-butanol; ethers such as tetrahydrofuran (THF) or dioxane; amides such as dimethylformamide (DMF) or N-methylpyrrolidone; or nitriles such as acetonitrile, or else, if desired, mixtures of these solvents with one another or mixtures with water. It can be favourable to add an acid-binding agent, for example an alkali metal or alkaline earth metal hydroxide, carbonate or bicarbonate or another alkali metal or alkaline earth metal salt of a weak acid, preferably a potassium, sodium or calcium salt, or to add an organic base such as triethylamine, dimethylaniline, pyridine or quinoline, or an excess of the amine component (3-(4-aminobutyl)-5-methoxyindole or IIIa). The reaction time is between a few minutes and 14 days, depending on the conditions used, and the reaction temperature is between about 0° and 150°, normally between 30° and 130°.

A compound of formula I can also be obtained by treating a precursor, in which hydrogen atoms have been replaced by one or more reducible groups and/or one or more additional C—C and/or C—N bonds, with a reducing agent, preferably at temperatures of between −80° and +250°, in the presence of at least one inert solvent.

Reducible groups (groups replaceable by hydrogen) are, in particular, oxygen in a carbonyl group, hydroxyl, arylsulfonyloxy (e.g. p-toluenesulfonyloxy), N-benzenesulfonyl, N-benzyl or O-benzyl.

In principle, compounds containing only one of the abovementioned groups or additional bonds, or compounds containing two or more of the abovementioned groups or additional bonds adjacent to one another, can be converted into I by reduction. This is preferably carried out using nascent hydrogen or complex metal hydrides or by means of a Wolff-Kishner reduction.

Preferred starting materials for the reduction conform to formula IV

Ind—L—W      IV wherein

Ind is a 5-methoxy-3-indolyl radical which can additionally be substituted in the 1-position by an arylsulfonyl group or a benzyl group, L is —$(CH_2)_4$— or a chain which corresponds to the radical —$(CH_2)_4$ except that one or more —$CH_2$— groups have been replaced by —CO— groups and/or one or more hydrogen atoms have been replaced by OH groups, W is

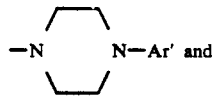

Ar' is a p-methoxyphenyl group which, in addition, can be monosubstituted or disubstituted by Cl or Br but wherein the following meanings cannot apply simultaneously: Ind=5-methoxy-3-indolyl, L=—$(CH_2)_4$ and W=p-methoxyphenylpiperazino.

In the compounds of formula IV, L is preferably —$(CH_2)_3$—CO— and also —CO—$(CH_2)_2$—CO—, —CO—$(CH_2)_3$—, —$CH_2$—CO—$CH_2CH_2$— or $CH_2$—$CH_2$—CO—$CH_2$—.

Compounds of formula IV can be prepared e.g. by reacting IIIa with a compound of formula V Ind—L—$X^1$      V wherein Ind, L and $X^1$ are as defined above, under the conditions indicated above for the reaction of II with III.

If nascent hydrogen is used as the reducing agent, this can be produced e.g. by treating metals with weak acids or with bases. Thus it is possible e.g. to use a mixture of zinc with an alkali metal hydroxide solution or a mixture of iron with acetic acid. It is also appropriate to use sodium or another alkali metal in an alcohol such as ethanol, isopropanol, butanol, amyl alcohol or isoamyl alcohol or phenol. It is also possible to use an aluminium-nickel alloy in aqueous-alkaline solution, ethanol being added if necessary. Sodium amalgam or aluminium amalgam in aqueous-alcoholic or aqueous solution is also suitable for producing the nascent hydrogen. The reaction can also be carried out in the heterogeneous phase, in which case it is convenient to use an aqueous phase and a benzene or toluene phase.

Other reducing agents which can be used to particular advantage are complex metal hydrides such as $LiAlH_4$, $NaBH_4$, diisobutylaluminium hydride or $NaAl(OCH_2CH_2OCH_3)_2H_2$, or diborane, catalysts such as $BF_3$, $AlCl_3$ or LiBr being added if desired. Solvents which are suitable for this purpose are, in particular, ethers such as diethyl ether, di-n-butyl ether, THF, dioxane, diglyme or 1,2-dimethoxyethane, and hydrocarbons such as benzene. Solvents which are suitable for reduction with $NaBH_4$ are primarily alcohols such as methanol or ethanol, as well as water and aqueous alcohols. Reduction by these methods is preferably carried out at temperatures of between −80° and +150°, especially of between about 0° and about 100°.

The reduction of —CO— groups in acid amides [e.g. N'-p-methoxyphenyl-4-(5-methoxy-3-indolyl)-butyropiperazide] to $CH_2$ groups can be carried out to particular advantage with $LiAlH_4$ in THF at temperatures of between about 0° and 66°. Arylsulfonyl protecting groups located in the 1-position of the indole ring can be simultaneously eliminated by reduction.

N-Benzyl groups can be eliminated by reduction with sodium in liquid ammonia.

It is also possible to reduce one or more carbonyl groups to $CH_2$ groups according to the Wolff-Kishner method, e.g. by treatment with anhydrous hydrazine in absolute ethanol, under pressure, at temperatures of between about 150° and 250°. A sodium alcoholate is advantageously used as the catalyst. The reduction can also be varied according to the Huang-Minlon method by carrying out the reaction with hydrazine hydrate in a high-boiling water-miscible solvent such as diethylene glycol or triethylene glycol, in the presence of an alkali such as sodium hydroxide. The reaction mixture is normally boiled for about 3-4 hours. The water is then distilled off and the hydrazone formed is decomposed at temperatures of up to about 200°. The Wolff-Kishner reduction can also be carried out with hydrazine in dimethyl sulfoxide at room temperature.

Compounds which conform to formula I except that one or more H atoms have been replaced by a solvolytically cleavable group can be solvolyzed, especially hydrolyzed, to give the compounds of formula I.

The starting materials for the solvolysis can be obtained for example by reacting IIIa with 1-Z-3-(4-X-butyl)-5-methoxyindoles (wherein Z is a solvolytically cleavable group and X is as defined). Thus, in particular, 1-acylindole derivatives (which conforms to I except that, in the 1-position of the indole radical, they contain an acyl group, preferably an alkanoyl, alkylsulfonyl or arylsulfonyl group having up to 10 C atoms in each case, such as methanesulfonyl, benzenesulfonyl or p-toluenesulfonyl) can be hydrolyzed to give I, e.g. in an acidic or, preferably, neutral or alkaline medium at temperatures of between 0° and 200°. Sodium, potassium or calcium hydroxide, sodium or potassium carbonate, or ammonia, are conveniently used as the base. The chosen solvents are preferably water; lower alcohols such as methanol or ethanol; ethers such as THF or dioxane; sulfones such as tetramethylenesulfone; or mixtures thereof, especially the mixtures containing water. Hydrolysis can also be carried out simply by treatment with water alone, especially at the boiling point.

A resultant base I can be converted with an acid into the corresponding acid addition salt. Acids which produce biocompatible salts are suitable for this reaction. Thus it is possible to use inorganic acids, e.g. sulfuric acid, hydrohalic acids such as hydrochloric acid or hydrobromic acid, phosphoric acids such as orthophosphoric acid, nitric acid and sulfamic acid, as well as organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and laurylsulfuric acid.

If desired, the free base I can be liberated from its salts by treatment with strong bases such as sodium or potassium hydroxide or sodium or potassium carbonate.

The invention further relates to the use of the compound I and its biocompatible salts for the manufacture of pharmaceutical preparations, especially by a non-chemical route. For this purpose, they can be converted into a suitable dosage form together with at least one excipient or adjunct and, if appropriate, in combination with one or more additional active ingredients.

The invention further relates to compositions, especially pharmaceutical preparations, containing the compound I and/or one of its biocompatible salts. These preparations can be used as drugs in human or veterinary medicine. Possible excipients are organic or inorganic substances which are suitable for enteral (e.g. oral), parenteral or topical administration and which do not react with the novel compounds, examples of such excipients being water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories are used in particular for enteral administration, solutions, preferably oily or aqueous solutions, as well as suspensions, emulsions or implants are used for parenteral administration, and ointments, creams or powders are used for topical administration. The novel compounds can also be lyophilized and the resulting lyophilizates used e.g. to manufacture injectable preparations. The preparations indicated can be sterilized and/or can contain adjuncts such as lubricants, preservatives, stabilizers and/or wetting agents, emulsifiers, salts for influencing the osmotic pressure, buffer substances, colorants, taste correctors and/or flavorings. If desired, they can also contain one or more additional active ingredients, e.g. one or more vitamins.

The compound I and its biocompatible salts can be used for the therapeutic treatment of the human or animal body and for controlling diseases, especially various types of anxiety including compulsive-obsessive disorders, psychoses, depressions, eating disorders, pain and hypertension. Furthermore, it can be used to treat side effects of neuroleptic therapy (extrapyramidal disorders) and side effects during antihypertensive therapy. The compounds can also be used in endocrinology and gynecology, and also for the therapeutic treatment of cerebral disorders (e.g. migraines), especially in geriatrics in a manner similar to certain ergot alkaloids.

In these treatments, the substances of the invention are normally administered analogously to known preparations (e.g. GR 43175; cf. Humphrey et al., Br. J. Pharmacol. 94 (1988), 1123–1132), preferably in dosages of between about 0.2 and 500 mg, especially of between 0.2 and 50 mg per dosage unit. The daily dosage is preferably between about 0.001 and 10 mg/kg of body weight. The low dosages (about 0.2 to 1 mg per dosage unit; about 0.001 to 0.005 mg/kg of body weight) are particularly suitable for use as anti-migraine preparations; dosages of between 10 and 50 mg per dosage unit are preferred for the other indications. However, the particular dose for each individual patient depends on a very wide variety of factors, for example the activity of the particular compound used, age, body weight, general state of health, sex, diet, time and method of administration, rate of excretion, drug combination and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 23 045.7, are hereby incorporated by reference.

In the following examples, "working-up in customary manner" means: water is added if necessary, extraction is carried out with methylene chloride, the organic phase is separated off, dried over sodium sulfate and filtered, the filtrate is evaporated and the residue is purified by chromatography on silica gel and/or by crystallization.

EXAMPLES

EXAMPLE 1

A solution of 23.75 g of 3-(4-chlorobutyl)-5-methoxyindole and 19.2 g of IIIa in 250 ml of acetonitrile is stirred at 20° for 12 hours and subjected to customary work-up, to give I; monohydrochloride, m.p. 236°–237.5°. Methanesulfonate, m.p. 180°–181°. Succinate, m.p. 154°. Fumarate, m.p. 181°. Maleate, m.p. 163°.

EXAMPLE 2

A mixture of 2.18 g of 3-(4-aminobutyl)-5-methoxyindole and 2.48 g of N,N-bis(2-chloroethyl)-p-methoxyaniline in 40 ml of acetone and 40 ml of water is boiled for 24 hours and subjected to customary work-up, to give I.

EXAMPLE 3

A suspension of 40.7 g of N'-p-methoxyphenyl-4-(5-methoxy-3-indolyl)butyropiperazide [m.p. 171–174; obtainable from 4-(5-methoxy-3-indolyl)butyric acid and IIIa in the presence of carbonyldiimidazole in THF at 20°] in 3 l of absolute THF is added dropwise with stirring and under an $N_2$ atmosphere to a suspension of 11.7 g of $LiALH_4$ (sic) in 1,000 ml of absolute THF, the mixture is boiled for 1 hour, cooled, decomposed using water and sodium hydroxide solution and subjected to customary work-up, to give I.

EXAMPLE 4

23.2 ml of a 70% solution of sodium bis(2-methoxyethoxy)aluminium dihydride in toluene is added with stirring and while passing $N_2$ into a suspension of 13.5 g of N'-p-methoxyphenyl-4-(5-methoxy-3-indolyl)-butyropiperazide in 200 ml of THF. During this addition, the temperature rises to 40°. The mixture is stirred for a further 16 hours and subjected to customary work-up, to give I.

EXAMPLE 5

5.19 g of 1-benzenesulfonyl-3-[4-(4-p-methoxyphenylpiperazino)butyl]-5-methoxyindole [obtainable from 1-benzenesulfonyl-3-(4-chlorobutyl)-5-methoxyindole and IIIa] are boiled with 1 g of KOH in 7 ml of water and 14 ml of ethanol for 16 hours, and the mixture is subjected to customary work-up to give I.

The following examples relate to pharmaceutical preparations containing the compound I or the acid addition salts thereof:

EXAMPLE A

Tablets

A mixture of I-monohydrochloride, 4 kg of lactose, 1.2 kg of potato starch, 0.2 kg of talc and 0.1 kg of magnesium stearate is compressed to tablets in conventional manner so that each tablet contains 10 mg of active ingredient.

EXAMPLE B

Coated Tablets

Tablets are formed by compression analogously to Example A and then covered in conventional manner with a coating of sucrose, potato starch, talc, tragacanth and colorant.

EXAMPLE C

Capsules 2 kg of I-methanesulfonate are filled into hard gelatin capsules in conventional manner so that each capsule contains 20 mg of the active ingredient.

EXAMPLE D

Ampoules

A solution of 1 kg of I-methanesulfonate in 300 l of double-distilled water is filtered under sterile conditions, filled into ampoules and lyophilized under sterile conditions and the ampoules are sealed under sterile conditions. Each ampoule contains 10 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 3-(4-(4-p-Methoxyphenylpiperazino)butyl)-5-methoxyindole or a salt thereof.

2. A compound of claim 1, comprising the free base of the compound or a biocompatible salt thereof.

3. A pharmaceutical preparation comprising a compound of claim 2 and a physiologically acceptable excipient.

4. A method of treating anxiety, comprising administering an anxiolytically effective amount of a compound of claim 2.

5. A method of treating psychosis, comprising administering an antipsychotically effective amount of a compound of claim 2.

6. A method of treating depression, comprising administering an antidepressively effective amount of a compound of claim 2.

7. A method of treating anorexia, comprising administering an antianorectically effective amount of a compound of claim 2.

8. A method of treating hypertension, comprising administering an antihypertensively effective amount of a compound of claim 2.

9. A method of inducing analgesia, comprising administering an analgesically effective amount of a compound of claim 2.

10. A method of treating migraine headaches, comprising administering an anti-migrainously effective amount of a compound of claim 2.

11. A method of inducing a serotonin-agonist effect, comprising administering a serotonin-agonistically effective amount of a compound of claim 2.

12. A method of inducing a serotonin-antagonist effect, comprising administering a serotonin-antagonistically effective amount of a compound of claim 2.

13. A method of treating extrapyrimidal disorders in neuroleptic, depression or psychosis therapy or of ameliorating side effects of antihypertensive therapies, comprising administering an amount of a compound of claim 2 effective to treat said disorders or to ameliorate said side effects.

14. A pharmaceutical preparation of claim 3, comprising between 0.2 and 500 mg of the compound.

15. A pharmaceutical preparation of claim 14, comprising between 0.2 and 50 mg of the compound.

* * * * *